United States Patent
Yano et al.

(10) Patent No.: US 11,548,878 B2
(45) Date of Patent: Jan. 10, 2023

(54) EMOPAMIL BINDING PROTEIN BINDING AGENT AND USE THEREOF

(71) Applicant: FUJIFILM Toyama Chemical Co., Ltd., Tokyo (JP)

(72) Inventors: Takeaki Yano, Toyama (JP); Kaori Miyamoto, Ashigarakami-gun (JP); Koichi Saito, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/760,512

(22) PCT Filed: Oct. 30, 2018

(86) PCT No.: PCT/JP2018/040283
§ 371 (c)(1),
(2) Date: Apr. 30, 2020

(87) PCT Pub. No.: WO2019/088083
PCT Pub. Date: May 9, 2019

(65) Prior Publication Data
US 2021/0198245 A1     Jul. 1, 2021

(30) Foreign Application Priority Data
Oct. 30, 2017 (JP) .............................. JP2017-209391

(51) Int. Cl.
*C07D 409/12* (2006.01)
*A61K 31/397* (2006.01)

(52) U.S. Cl.
CPC ........ *C07D 409/12* (2013.01); *C07B 2200/05* (2013.01)

(58) Field of Classification Search
CPC .......................... C07D 409/12; A61K 31/397
See application file for complete search history.

(56) References Cited

U.S. PATENT DOCUMENTS

| | | | |
|---|---|---|---|
| 6,489,481 B1 | 12/2002 | Keith et al. | |
| 7,087,594 B2 * | 8/2006 | Saitoh | A61P 25/00 514/210.17 |
| 8,119,625 B2 * | 2/2012 | Iwakami | A61K 31/397 514/210.19 |
| 10,238,632 B2 * | 3/2019 | Yano | A61P 9/10 |
| 2005/0070521 A1 | 3/2005 | Saitoh et al. | |
| 2005/0250843 A1 | 11/2005 | Nakada et al. | |
| 2006/0194781 A1 | 8/2006 | Saitoh et al. | |
| 2006/0205709 A1 | 9/2006 | Kimura et al. | |
| 2009/0093453 A1 | 4/2009 | Iwakami et al. | |
| 2011/0224180 A1 | 9/2011 | Pruss et al. | |
| 2012/0028953 A1 | 2/2012 | Roughley et al. | |
| 2015/0045345 A1 | 2/2015 | Inaba et al. | |
| 2015/0166472 A1 * | 6/2015 | Kim | A61K 9/06 514/64 |
| 2015/0203472 A1 | 7/2015 | Ceccarelli et al. | |
| 2016/0324851 A1 | 11/2016 | Friedhoff et al. | |
| 2017/0129915 A1 | 5/2017 | Tohda et al. | |
| 2017/0165227 A1 | 6/2017 | Takahashi et al. | |
| 2018/0153855 A1 | 6/2018 | Yano | |
| 2018/0369194 A1 | 12/2018 | Kano et al. | |
| 2020/0085787 A1 | 3/2020 | Kobayashi et al. | |
| 2020/0108048 A1 * | 4/2020 | Kobayashi | A61P 25/28 |
| 2020/0137880 A1 * | 4/2020 | Li | H05K 1/0218 |
| 2020/0155505 A1 * | 5/2020 | Kobayashi | A61K 31/397 |
| 2020/0215030 A1 * | 7/2020 | Kobayashi | A61K 9/0053 |
| 2021/0137880 A1 | 5/2021 | Kobayashi et al. | |

FOREIGN PATENT DOCUMENTS

| | | |
|---|---|---|
| EP | 1 437 353 A1 | 7/2004 |
| EP | 3 100 725 A1 | 12/2016 |
| EP | 3 632 431 A1 | 4/2020 |

(Continued)

OTHER PUBLICATIONS

Chemical Abstracts Registry No. 519187-30-5, indexed in the Registry file on STN CAS Online May 23, 2003. (Year: 2003).*
Marquer et al., Increasing membrane cholesterol of neurons in culture recapitulates Alzheimer's disease early phenotypes. Mol Neurodegeneration 9, 60 (2014). https://doi.org/10.1186/1750-1326-9-60. (Year: 2014).*
Extended European Search Report dated Jul. 3, 2020, from the European Patent Office in European application No. 18873445.3.
Silve et al., "Emopamil-binding Protein, a Mammalian Protein That Binds a Series of Structurally Diverse Neuroprotective Agents, Exhibits Δ8-Δ7 Sterol Isomerase Activity in Yeast", The Journal of Biological Chemistry, Sep. 13, 1996, vol. 271, No. 37, pp. 22434-22440 (8 pgs. total).

(Continued)

*Primary Examiner* — Laura L Stockton
(74) *Attorney, Agent, or Firm* — Sughrue Mion, PLLC

(57) ABSTRACT

Required are: a compound having high affinity for an emopamil binding protein; and a method for activating or inhibiting the emopamil binding protein, using such a compound. According to the present invention, provided is an emopamil binding protein binding agent comprising an alkyl ether derivative represented by the following formula [1] or a salt thereof:

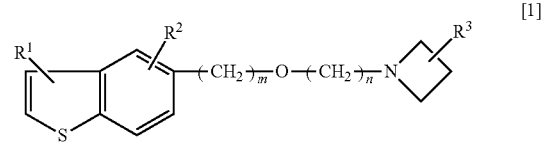

wherein $R^1$ and $R^2$, which are the same or different, each represent a hydrogen atom, a halogen atom, an optionally substituted $C_{1-6}$ alkyl group, an optionally substituted aryl group, etc.; $R^3$ represents an optionally protected hydroxyl group, etc.; and m and n, which are the same or different, each represent an integer of 1 to 6.

5 Claims, 1 Drawing Sheet

(56) References Cited

FOREIGN PATENT DOCUMENTS

| JP | 2002-528489 | A | 9/2002 | | |
|---|---|---|---|---|---|
| JP | 2011-513374 | A | 4/2011 | | |
| KR | 10-2008-0111131 | A | 12/2008 | | |
| RU | 2496784 | C2 | 10/2013 | | |
| RU | 2015112914 | A | 11/2016 | | |
| WO | WO-99/11293 | A1 | * | 3/1999 | ............ A61K 48/00 |
| WO | 03/035647 | A1 | 5/2003 | | |
| WO | 03/105830 | A1 | 12/2003 | | |
| WO | 2007/125913 | A1 | 11/2007 | | |
| WO | 2011/057199 | A1 | 5/2011 | | |
| WO | 2013/125617 | A1 | 8/2013 | | |
| WO | 2015/115582 | A1 | 8/2015 | | |
| WO | 2015/191506 | A2 | 12/2015 | | |
| WO | 2016/051799 | A1 | 4/2016 | | |
| WO | 2016/124508 | A1 | 8/2016 | | |
| WO | 2016/199878 | A1 | 12/2016 | | |
| WO | 2017/111005 | A1 | 6/2017 | | |

OTHER PUBLICATIONS

Derry et al., "Mutations in a Δ8-Δ7 sterol isomerase in the tattered mouse and X-linked dominant chondrodysplasia punctata", Nature Genetics, Jul. 1999, vol. 22, pp. 286-290.

Bae et al., "Cholesterol biosynthesis from lanosterol: molecular cloning, chromosomal localization, functional expression and liver-specific gene regulation of rat sterol Δ8-isomerase, a cholesterogenic enzyme with multiple functions", Biochem. J., 2001, vol. 353, pp. 689-699.

Moebius et al., "Identification of a 27-κDa High Affinity Phenylalkylamine-Binding Polypeptide as the sigma 1 Binding Site by Photoaffinity Labeling and Ligand-Directed Antibodies", Molecular Pharmacology, 1993, vol. 44, No. 5, pp. 966-971 (8 pgs. total).

Laggner et al., "Discovery of High-Affinity Ligands of sigma1 Receptor, ERG2, and Emopamil Binding Protein by Pharmacophore Modeling and Virtual Screening", J. Med. Chem., 2005, vol. 48, No. 15, pp. 4754-4764.

Berardi et al., "Novel 4-(4-Aryl)cyclohexyl-1-(2-pyridyl)piperazines as Δ8-Δ7 Sterol Isomerase (Emopamil Bonding Protein) Selective Ligands with Antiproliferative Activity", J. Med. Chem., 2008, vol. 51, No. 23, pp. 7523-7531.

International Search Report dated Jan. 29, 2019, issued by the International Searching Authority in application No. PCT/JP2018/040283.

Written Opinion dated Jan. 29, 2019, issued by the International Searching Authority in application No. PCT/JP2018/040283.

International Preliminary Report on Patentability dated May 5, 2020, issued by the International Bureau in application No. PCT/JP2018/040283.

"2012 Alzheimer's Disease Facts and Figures", Alzheimer's Association, 2012 (72 pages total); http://www.alz.org/downloads/facts_figures_2012.pdf.

Colovic et al., "Acetylcholinesterase inhibitors: Pharmacology and Toxicology", Current Neuropharmacology, 2013, vol. 11, pp. 315-335.

Communication dated Aug. 11, 2021 from the Canadian Patent Office in Canadian Application No. 3,067,458, corresponds to U.S. Appl. No. 16/617,607.

Communication dated Aug. 17, 2021 from the Mexican Patent Office in Mexican Application No. MX/a/2019/014306, corresponds to U.S. Appl. No. 16/617,607.

Communication dated Aug. 4, 2021 from the Canadian Patent Office in Canadian Application No. 3,067,456, corresponds to U.S. Appl. No. 16/617,552.

Communication dated Dec. 8, 2020, issued by the Korean Intellectual Property Office in Korean Application No. 10-2019-7035347.

Communication dated Dec. 8, 2020, issued by the Korean Intellectual Property Office in Korean Application No. 10-2019-7035348.

Communication dated Dec. 9, 2020, issued by the Korean Intellectual Property Office in Korean Application No. 10-2019-7035349.

Communication dated Dec. 9, 2020, issued by the Korean Intellectual Property Office in Korean Application No. 10-2019-7035350.

Communication dated Feb. 3, 2021 issued by the Indian Patent Office in Application No. 201947049390.

Communication dated Feb. 3, 2021 issued by the Indian Patent Office in Application No. 201947049400.

Communication dated Jan. 27, 2021 issued by the Canadian Patent Office in Application No. 3,067,453.

Communication dated Jan. 27, 2021 issued by the Canadian Patent Office in Application No. 3,067,455.

Communication dated Jan. 27, 2021 issued by the Canadian Patent Office in Application No. 3,067,456.

Communication dated Jan. 29, 2021 issued by the Canadian Patent Office in Application No. 3,067,458.

Communication dated Jan. 8, 2021 issued by the Indian Patent Office in application No. 201947049392.

Communication dated Jan. 8, 2021, issued by the Indian Intellectual Property Office in Indian Application No. 201947049401.

Communication dated May 11, 2020 from European Patent Office in EP Application No. 18810759.3.

Communication dated May 7, 2020 from European Patent Office in EP Application No. 18810520.9.

Decision under section 15 dated Feb. 23, 2021, issued in Indian Application No. 201947049401.

Decision under section 15 dated Mar. 22, 2021 issued in the Indian patent application No. 201947049390.

Decision under section 15 dated Mar. 22, 2021 issued in the Indian patent application No. 201947049392.

"Epidemiological studies on Alzheimer's disease in Japan", Japanese Journal of Clinical Medicine, 2008, vol. 66 (Extra ed. 1), pp. 23-27 (5 pages total).

Extended European Search Report dated May 11, 2020 in European Application No. 18809579.8.

Extended European Search Report dated May 11, 2020 in European Application No. 18809739.8.

Extended European Search Report dated May 13, 2020 in European Application No. 18809110.2.

Fujifilm Corp., "II stage clinical experiment in the United States for Alzheimer's dementia therapeutic drug 'T-817MA': drastically restricting, with statistical significant difference, progress of deterioration in cognitive function with respect to patient group having this innovative two effects of reducing phosphorylation tau in cerebrospinal fluid and restricting hippocampal atrophy in brain", News release, Jul. 19, 2017 (1 page total).

Fukushima et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734 (5 pages total).

Fukushima, "Pharmacological properties of T-817MA, a novel neurotrophic agent, for treatment of Alzheimer's disease", Folia Pharmacologica Japonica, 2010, vol. 136, pp. 11-14 (2 pages total).

Grimmer et al., "Beta Amyloid in Alzheimer's Disease: Increased Deposition in Brain Is Reflected in Reduced Concentration in Cerebrospinal Fluid", Biol. Psychiatry, 2009, vol. 65, No. 11, pp. 927-934 (17 pages total).

Healthline, "Brain Atrophy (Cerebral Atrophy)", updated Mar. 29, 2019 https://www.healthline.com/health/brain-atrophy.

Hirata et al., "A Novel Neurotrophic Agent, T-817MA [1-{3-[2-(1-Benzothiopen-5-yl) Ethoxy] Propyl}-3-azetidinol Maleate], Attenuates Amyloid-beta-Induced Neurotoxicity and Promotes Neurite Outgrowth in Rat Cultured Central Nervous System Neurons", The Journal of Pharmacology and Experimental Therapeutics, vol. 314, No. 1, pp. 252-259, 2005 (8 pages total).

Horig et al., "From bench to clinic and back: Perspective on the 1st IQPC Translational Research conference", Journal of Translational Medicine, 2004, vol. 2, No. 44, pp. 1-8.

International Preliminary Report on Patentability dated Dec. 3, 2019 in International Application No. PCT/JP2018/021222.

International Preliminary Report on Patentability dated Dec. 3, 2019 in International Application No. PCT/JP2018/021223.

International Preliminary Report on Patentability dated Dec. 3, 2019 in International Application No. PCT/JP2018/021224.

(56) References Cited

OTHER PUBLICATIONS

International Preliminary Report on Patentability dated Dec. 3, 2019 in International Application No. PCT/JP2018/021225.
International Preliminary Report on Patentability dated Dec. 3, 2019 in International Application No. PCT/JP2018/021226.
International Search Report dated Jul. 24, 2018 in International Application No. PCT/JP2018/021223.
International Search Report dated Jul. 24, 2018 in International Application No. PCT/JP2018/021224.
International Search Report dated Jul. 24, 2018 in International Application No. PCT/JP2018/021225.
International Search Report dated Jul. 24, 2018 in International Application No. PCT/JP2018/021226.
International Search Report dated Sep. 4, 2018 in International Application No. PCT/JP2018/021222.
Jack Jr. et al., "Tracking pathophysiological processes in Alzheimer's disease: an updated hypothetical model of dynamic biomarkers", Lancet Neurology, Feb. 2013, vol. 12, No. 2, pp. 207-216 (10 pages total).
Jagust, "Is amyloid-β harmful to the brain? Insights from human imaging studies", Brain, 2016, vol. 139, pp. 23-30.
Japanese Journal of Clinical Psychopharmacology, 2011, vol. 14, No. 7, pp. 1123-1129.
Japanese Journal of Clinical Psychopharmacology, 2012, vol. 15, No. 3, pp. 311-321.
Japanese Journal of Geriatrics, 2013, vol. 50, No. 1, pp. 1-8 (8 pages total).
Kawasaki et al., "A Neuroprotective Agent, T-817MA (1-{3-[2-(1-benzothiophen-5-yl)ethoxy]propyl} azetidin-3-ol Maleate), Prevents 1-methyl-4-phenyl-1,2,3,6-tetrahydropyridine-induced Neurotoxicity in Mice", Neuropharmacology, vol. 55, Issue 5, Oct. 2008, pp. 654-660, Abstract only.
Kimura et al., "T-817MA, a neurotrophic agent, ameliorates the deficits in adult neurogenesis and spatial memory in rats infused i.c.v. with amyloid-beta peptide", British Journal of Pharmacology, 2009, vol. 157, pp. 451-463 (13 pages total).
Kolobov et al., "Modern Pharmacological Models of Alzheimer's Disease", Original Articles, Experimental Neurology, 2014, vol. 8, No. 3, pp. 38-44 (32 pages total).
Lo et al., "Longitudinal Change of Biomarkers in Cognitive Decline", Archives of Neurology, 2011, vol. 68, No. 10, pp. 1257-1266 (10 pages total).
Mascalchi et al., "Progression of Brain Atrophy in Spinocerebellar Ataxia Type 2: A Longitudinal Tensor-Based Morphometry Study", PLOS One, 2014, vol. 9, Issue 2, pp. 1-7, e89410.
McKhann et al., "The diagnosis of dementia due to Alzheimer's disease: Recommendations from the National Institute on Aging-Alzheimer's Association workgroups on diagnostic guidelines for Alzheimer's disease", Alzheimer's Dement., May 2011, vol. 7, No. 3, pp. 263-269, (52 pages total).
Moreno et al., "Blocking effects of human tau on squid giant synapse transmission and its prevention by T-817MA", Frontiers in Synaptic Neuroscience, May 2011, vol. 3, Article 3, pp. 1-8 (8 pages total).
Nakagawa et al., "T-817MA, A Newly Developing Anti-Alzheimer's Agent, Protects Neurons and Recovers Memory Impairment in Amyloid B-Infused Rats and P301L Tau mutated Mice", Alzheimer's & Dementia: The Journal of the Alzheimer's Association, Jul. 1, 2005, XP027823394, p. 193, vol. 1, No. 1, p. S69-S70 (total 2 pages).
Nguyen et al., "Ameliorative Effects of a Neuroprotective Agent, T-817MA, on Place Learning Deficits Induced by Continuous Infusion of Amyloid-β Peptide (1-40) in Rats", Hippocampus, 2007, vol. 17, pp. 443-455.
Notice of Allowance dated Sep. 28, 2021 in U.S. Appl. No. 16/617,660.
Notice of Final Rejection dated Aug. 24, 2021 by the Korean Patent Office in Korean Application No. 10-2019-7035348, corresponds to U.S. Appl. No. 16/617,660.

Office Action dated Apr. 27, 2020 from Russian Patent Office in RU Application No. 2019138166/04.
Office Action dated Feb. 17, 2021, issued in Russian Application No. 2019138166/04.
Office Action dated Jun. 1, 2021 issued in the Singapore patent application No. 11201911512S.
Office Action dated Jun. 1, 2021 issued in the Singapore patent application No. 11201911515Q.
Office Action dated Jun. 1, 2021 issued in the Singapore patent application No. 11201911519U.
Office Action dated Jun. 1, 2021 issued in the Singapore patent application No. 11201911520U.
Office Action dated Oct. 23, 2020 in Russian Application No. 2019138538.
Office Action dated Sep. 25, 2020 in Russian Application No. 2019138166.
Office Action dated Aug. 10, 2020 in Australian Application No. 2018276638.
Office Action dated Aug. 14, 2020 in Australian Application No. 2018277981.
Office Action dated Aug. 17, 2020 in Australian Application No. 2018277983.
Office Action dated Aug. 19, 2021 in U.S. Appl. No. 16/617,584.
Office Action dated Aug. 21, 2020 in Australian Application No. 2018277982.
Office Action dated Jul. 21, 2021 in New Zealand Application No. 759585, corresponds to U.S. Appl. No. 16/617,739.
Office Action dated Jul. 21, 2021 in New Zealand Application No. 759647, corresponds to U.S. Appl. No. 16/617,660.
Office Action dated Jul. 21, 2021 in New Zealand Application No. 759657, corresponds to U.S. Appl. No. 16/617,552.
Office Action dated Jul. 22, 2021 in New Zealand Application No. 759662, corresponds to U.S. Appl. No. 16/617,607.
Office Action dated Jul. 3, 2020 in Russian Application No. 2019138699.
Office Action dated Jun. 10, 2021 in U.S. Appl. No. 16/617,660.
Office Action dated Jun. 23, 2021 in U.S. Appl. No. 16/617,607.
Office Action dated Jun. 23, 2021 in U.S. Appl. No. 16/617,739.
Office Action dated Jun. 25, 2021 in Korean Application No. 10-2019-7035347.
Office Action dated Mar. 2, 2020 in Russian Application No. 2019138164.
Office Action dated May 26, 2020 in Indian Application No. 201947049390.
Office Action dated May 26, 2020 in Indian Application No. 201947049392.
Office Action dated May 26, 2020 in Indian Application No. 201947049400.
Office Action dated May 26, 2020 in Indian Application No. 201947049401.
Office Action dated May 29, 2020 in Russian Application No. 2019138538.
Press Release by Seed Planning (Dec. 28, 2010) (3 pages total); http://www.seedplanning.co.jp/press/2010/2010122801.html.
Proceedings of the Annual Meeting of the Japanese Research Group on Senile Dementia, 2010, vol. 15, pp. 79-81 (3 pages total).
Quinti et al., "A Novel Drug-Screening Platform in Microglial Cells Identifies Potential AD Drugs", Alzheimer's & Dementia: The journal of the Alzheimer's Association, Jul. 19, 2017, XP085218817, p. 4-404, vol. 1, No. 13, p. P1485 (total 1 page).
Sarva et al., "Treatment Options in Degenerative Cerebellar Ataxia: A Systematic Review", Movement Disorders Clinical Practice, 2014, vol. 1, pp. 291-298.
Schafer et al., "Failure is an option: learning from unsuccessful proof-of concept trials", Drug Discovery Today, 2008, Vo. 13, pp. 913-916.
Schneider et al., "A Phase 2 Multicenter, Randomized, Placebo-Controlled Trial to Evaluate the Efficacy and Safety of Edonerpic (T-817) in Patients with Mild to Moderate Alzheimer's Disease", Alzheimer's & Dementia: The journal of the Alzheimer's Association, Jul. 19, 2017, p. 4-573. vol. 13, No. 7, XP085218926, p. P1572 (total 1 page).

(56) References Cited

OTHER PUBLICATIONS

Shigemori et al., "The factorial structure of the mini mental state examination (MMSE) in Japanese dementia patients", BMC Geriatrics, 2010, vol. 10, Issue 36, pp. 1-7.
SIM integrated internal medicine understood through anatomy and pathophysiology 10 : Neurology Spinocerebellar Degeneration, May 30, 2013 (12 pages total).
Written Opinion dated Jul. 24, 2018 in International Application No. PCT/JP2018/021223.
Written Opinion dated Jul. 24, 2018 in International Application No. PCT/JP2018/021224.
Written Opinion dated Jul. 24, 2018 in International Application No. PCT/JP2018/021225.
Written Opinion dated Jul. 24, 2018 in International Application No. PCT/JP2018/021226.
Written Opinion dated Sep. 4, 2018 in International Application No. PCT/JP2018/021222.
Yamaguchi et al., "T-817MA, a neurotrophic compound, reverses Aβ neurotoxicity and promotes neurite outgrowth through PI3-Kinase pathway in rat primary neurons", Abstract of the Annual Meeting of the Society for Neuroscience, Nov. 8, 2003, XP008135922, pp. 1-2 (total 2 pages).
Yano et al., "SIGMA-1 Receptor is a Molecular Target for Novel Neuropretectant T-817MA", Alzheimer's & Dementia: The Journal of the Alzheimer's Association, Jul. 1, 2015, XP029355158, p. 4-210, vol. 11, No. 7, p. P861 (total 1 page).
Sugimoto, "Development of Anti-Alzheimer's Disease Drug Based on Beta-Amyloid Hypothesis", Yakugaku Zasshi, 2010, vol. 130, No. 4, pp. 521-526 (6 pages total).
Takamura et al., "Effects of the neurotrophic agent T-817MA on oligomeric amyloid-beta-induced deficits in long-term potentiation in the hippocampal CA1 subfield", Neurobiology of Aging, 2014, vol. 35, pp. 532-536 (5 pages total).
Tosun et al., "Relationship Between Regional Brain Amyloid-β Deposition and Brain Atrophy Rates in Mild Cognitive Impairment", Alzheimer's & Dementia: The Journal of the Alzheimer's Association, Jul. 1, 2010, XP027440489, vol. 6, No. 4, p. e15 (total 1 page).
Tosun et al., "Spatial patterns of brain amyloid-b burden and atrophy rate associations in mild cognitive impairment", Brain, 2011, vol. 134, pp. 1077-1088.
Uehara et al., "T-817MA, a novel neurotrophic agent, ameliorates loss of GABAergic parvalbumin-positive neurons and sensorimotor gating deficits in rats transiently exposed to MK-801 in the neonatal period", Journal of Psychiatric Research, vol. 46, No. 5, pp. 622-629, 2012 (8 pages total).
Office Action dated Jul. 2, 2021 in U.S. Appl. No. 16/617,552.
Blennow, "Cerebrospinal Fluid Protein Biomarkers for Alzheimer's Disease", The American Society for Experimental NanoTherapeutics, 2004, vol. 1, pp. 213-225.
Grigorenko et al., "Molecular Basics of Alzheimer's Disease", Molekulyarnaya Biologiya, 2007, vol. 41, No. 2, pp. 331-345.
Lemere et al., "Sequence of Deposition of Heterogeneous Amyloid β-Peptides and APO E in Down Syndrome: Implications for Initial Events in Amyloid Plaque Formation", Neurobiology of Disease, 1996, vol. 3, pp. 16-32, Article No. 0003.
Office Action dated Jun. 10, 2021 in Russian Application No. 2019138538.
Office Action dated Jun. 10, 2021 in Mexican Application No. MX/a/2019/014306.
Manto et al., "Animal Models of Human Cerebellar Ataxias: a Cornerstone for the Therapies of the Twenty-First Century", Cerebellum, 2009, vol. 8, pp. 137-154.
Office Action dated Jul. 13, 2021 in Japanese Application No. 2019-521350.
Shimohama et al., Journal of Japan Senile Medicine, vol. 50, No. 1, pp. 50:1-50:8.
Office Action dated Nov. 9, 2021 in U.S. Appl. No. 16/617,607.
Office Action dated Nov. 4, 2021 in Mexican Application No. MX/a/2019/014306, corresponds to U.S. Appl. No. 16/617,607.

Office Action dated Jun. 24, 2021 in Korean Application No. 10-2019-7035349.
Office Action dated Jun. 24, 2021 in Korean Application No. 10-2019-7035350.
Office Action dated Jun. 25, 2021 in Korean Application No. 10-2019-7035348.
Busciglio et al., "Altered Metabolism of the Amyloid β Precursor Protein Is Associated with Mitochondrial Dysfunction in Down's Syndrome", Neuron, 2002, vol. 33, pp. 677-688 (12 pages total).
Chetelat et al., "Relationship between Atrophy and β-Amyloid Deposition in Alzheimer Disease", Ann Neurol, 2010, vol. 67, pp. 317-324 (8 pages total).
Office Action dated Dec. 14, 2021 in Korean Application No. 10-2019-7035349, corresponds to U.S. Appl. No. 16/617,552.
Office Action dated Dec. 14, 2021 in Korean Application No. 10-2019-7035350, corresponds to U.S. Appl. No. 16/617,607.
Office Action dated Dec. 20, 2021 in Korean Application No. 10-2019-7035347, corresponds to U.S. Appl. No. 16/617,739.
Aisen et al., "On the path to 2025: understanding the Alzheimer's disease continuum", Alzheimer's Research & Therapy, 2017, vol. 9, No. 60, pp. 1-10 (10 pages total).
Head et al., "Alzheimer's Disease in Down Syndrome", Eur J Neurodegener Dis., 2012, vol. 1, No. 3, pp. 353-364 (16 pages total).
Office Action dated Feb. 14, 2022 in U.S. Appl. No. 16/617,607.
Office Action dated Jan. 25, 2022 in Russian Application No. 2019138538, corresponds to U.S. Appl. No. 16/617,607.
Office Action dated Jan. 28, 2022 in U.S. Appl. No. 16/617,552.
Office Action dated Dec. 9, 2021 in Mexican Application No. MX/a/2019/014300, corresponding to U.S. Appl. No. 16/617,552.
Decision of Refusal dated Nov. 30, 2021 from the Japanese Patent Office in Japanese Application No. 2019-521350, corresponds to U.S. Appl. No. 16/617,552.
A. Sugiyama and H. Shimada, "Tau PET Imaging for Dementia in Clinical Practice", Radioisotopes, vol. 65, No. 12, pp. 517-522 (Japan Radioisotope Association, 2016) (6 pages total).
Naoji Amano, "Neurodegenerative Diseases and Tauopathy", Shinshu Journal, 2002, vol. 50, No. 3, pp. 113-120 (8 pages total).
Y. Soeda and A. Takashima, "Development of disease modifying drugs for dementia—focusing on anti-tau drugs", Clinical Neurology, vol. 54, pp. 1178-1180 (2014) (3 pages total).
Y. Yoshiyama, Nippon Rinsho, Japanese Journal of Clinical Medicine, vol. 69, Suppl. 8, pp. 262-266 (2011) (5 pages total).
H. Takahashi, "Animal models of Alzheimer's disease for preclinical research", Folia Pharmacol. Jpn., vol. 136, No. 1, pp. 6-10 (2010) (5 pages total).
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Pharma and Toxicology, 2005, pp. 1-27 (30 pages total).
Office Action dated Dec. 15, 2021 in U.S. Appl. No. 16/617,739.
Notice of Allowance dated Dec. 15, 2021 in U.S. Appl. No. 16/617,660.
Notice of Allowance dated Mar. 14, 2022 in U.S. Appl. No. 16/617,584.
Office Action dated Feb. 18, 2022 in Canadian Application No. 3,067,456, corresponds to U.S. Appl. No. 16/617,552.
Notice of Allowance dated Apr. 1, 2022 in U.S. Appl. No. 16/617,739.
Office Action dated Mar. 2, 2022 in Mexican Application No. MX/a/2019/014302, corresponds to U.S. Appl. No. 16/617,660.
Office Action dated Mar. 1, 2022 in Mexican Application No. MX/a/2019/014306, corresponds to U.S. Appl. No. 16/617,607.
Office Action dated Mar. 3, 2022 in Mexican Application No. MX/a/2019/014310, corresponds to U.S. Appl. No. 16/617,739.
Notice of Allowance dated Apr. 4, 2022 in U.S. Appl. No. 16/617,607.
Office Action dated Apr. 4, 2022 in New Zealand Application No. 759662, corresponds to U.S. Appl. No. 16/617,607.
Office Action dated Mar. 31, 2022 in Korean Application No. 10-2019-703530, corresponds to U.S. Appl. No. 16/617,607.
Communication dated Apr. 12, 2022 from the Korean Patent Office in Korean Application No. 10-2019-7035347, corresponds to U.S. Appl. No. 17/617,739.

(56) References Cited

OTHER PUBLICATIONS

Communication dated Apr. 7, 2022 from the Korean Patent Office in Korean Application No. 10-2019-7035349, corresponds to U.S. Appl. No. 16/617,552.
Office Action dated May 10, 2022 in Japanese Application No. 2019-521347, corresponds to U.S. Appl. No. 16/617,584.
Office Action dated May 6, 2022 in Chinese Application No. 201880035394.0, corresponds to U.S. Appl. No. 16/617,739.
Office Action dated May 6, 2022 in Chinese Application No. 201880035501.X, corresponds to U.S. Appl. No. 16/617,660.
Office Action dated May 6, 2022 in Chinese Application No. 201880035503.9, corresponds to U.S. Appl. No. 16/617,552.
Office Action dated May 6, 2022 in Chinese Application No. 201880035521.7, corresponds to U.S. Appl. No. 16/617,607.
Office Action dated May 10, 2022 in Japanese Application No. 2019-521348, corresponds to U.S. Appl. No. 16/617,739.
Reconsideration Report by Examiner dated Apr. 28, 2022 in Japanese Application No. 2019-521350, corresponds to U.S. Appl. No. 16/617,552.
Office Action dated May 24, 2022 in Japanese Application No. 2019-521349, corresponds to U.S. Appl. No. 16/617,660.
Peng Ying et al., "Progress of clinical trials in Alzheimer's disease drugs", Acta Pharmaceutica Sinica, 2016, vol. 51, No. 8, pp. 1185-1195 (11 pages total).
Yuli Xie, Pharmaceutical and Clinical Research, 2011, vol. 19, No. 1, pp. 1-7 (7 pages total).
Buccarello et al., "Sex Impact on Tau-Aggregation and Postsynaptic Protein Levels in the P301L Mouse Model of Tauopathy" Journal of Alzheimer's Disease, 2017, vol. 56, No. 4, pp. 1279-1292 (27 pages total).
Office Action dated Jun. 6, 2022 in U.S. Appl. No. 16/617,552.
Office Action dated Jun. 7, 2022 in Japanese Application No. 2019-521351, corresponds to U.S. Appl. No. 16/617,607.
Zheng et al., "Amyloid ß Peptide induces Tau Phosphorylation and Loss of Cholinergic Neurons in Rat Primary Septal Cultures", Neuroscience, 2002, vol. 115, No. 1, pp. 201-211 (11 pages total).
Office Action dated Apr. 12, 2022 in Israeli Application No. 270910, corresponds to U.S. Appl. No. 16/617,660.
Office Action dated Jul. 26, 2022 in Brazilian Application No. BR1120190249834, corresponds to U.S. Appl. No. 16/617,607.
Allowance dated Aug. 15, 2022 in U.S. Appl. No. 16/617,584.
Office Action dated Aug. 15, 2022 in U.S. Appl. No. 16/617,739.
Office Action dated Aug. 16, 2022 in U.S. Appl. No. 16/617,607.
Office Action dated Jun. 26, 2022 in Israeli Application No. 270912, corresponds to U.S. Appl. No. 16/617,552.
Office Action dated Jun. 27, 2022 in Israeli Application No. 270922, corresponds to U.S. Appl. No. 16/617,739.
Office Action dated Aug. 29, 2022 in Korean Application No. 10-2022-7022765, corresponds to U.S. Appl. No. 16/617,552.
Office Action dated Aug. 29, 2022 in Korean Application No. 10-2022-7022766, corresponds to U.S. Appl. No. 16/617,552.
Office Action issued in Brazilian Application No. BR1120190248811 dated Sep. 13, 2022.
Office Action issued in Brazilian Application No. BR1120190245810 dated Sep. 13, 2022.
Office Action dated Oct. 18, 2022 by Japan Patent Office in Japanese Application No. 2019-550404.
Office Action dated Nov. 8, 2022 in Japanese Application No. 2019-521351, corresponds to U.S. Appl. No. 16/617,607.
Hanney et al., "Memantine for dementia in adults older than 40 years with Down's syndrome (Meadows): a randomised, double-blind, placebo-controlled trial", Lancet, 2012, vol. 379, pp. 528-536 (9 pages total).
Livingstone et al., "Pharmacological interventions for cognitive decline in people with Down syndrome (Review)", Cochrane Database of Systematic Reviews, 2015, Issue 10, Art. No. CD011546 (57 pages total).
Office Action dated Nov. 15, 2022 in Japanese Application No. 2019-521347, corresponds to U.S. Appl. No. 16/617,584.
Office Action dated Nov. 15, 2022 in Japanese Application No. 2019-521348, corresponds to U.S. Appl. No. 16/617,739.

* cited by examiner

[Fig. 1]
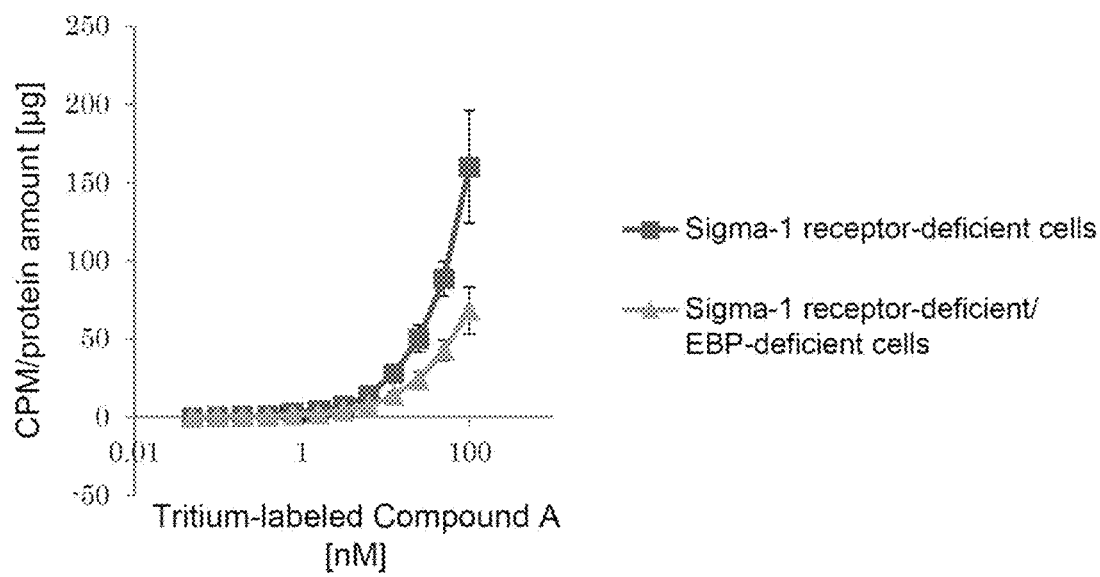
[Fig. 2]
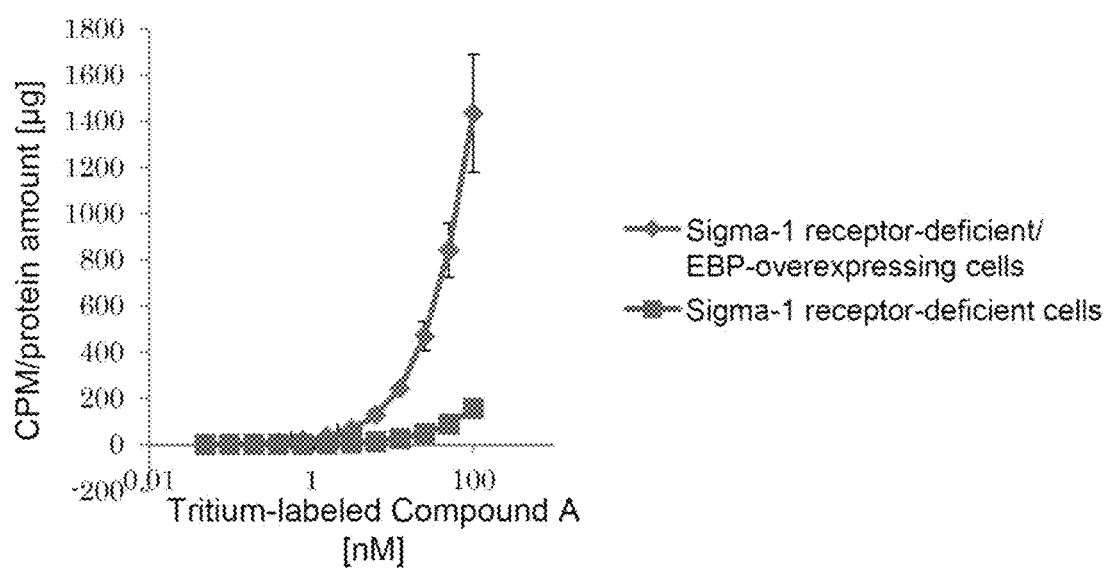

EMOPAMIL BINDING PROTEIN BINDING AGENT AND USE THEREOF

CROSS REFERENCE TO RELATED APPLICATIONS

This application is a National Stage of International Application No. PCT/JP2018/040283, filed Oct. 30, 2018, claiming priority to Japanese Patent Application No. 2017-209391, filed Oct. 30, 2017.

TECHNICAL FIELD

The present invention relates to an alkyl ether derivative that is useful as an emopamil binding protein (hereinafter also referred to as "EBP") binding agent, or a salt thereof. In addition, the present invention also relates to a method for activating or inhibiting EBP, using the alkyl ether derivative or a salt thereof.

BACKGROUND ART

EBP is a membrane protein that is mainly present in the endoplasmic reticulum, and exhibits D8-D7 sterolisomerase activity (Non-Patent Document 1). EBP is also present in the nucleus in the central nervous system and multiple types of central nervous cells (e.g., astrocyte, microglia, and oligodendrocyte), and thus, it is considered that EBP has a role other than the role of sterolisomerase.

It has been reported that a mutation in EBP is one factor for X linked dominant Conradi-Hunermann chondrodysplasia punctata (CDPX2) (Non-Patent Document 2). CDPX2 may cause asymmetric forelimb malformation, cataract, alopecia, congenital ichthyosis, dermatrophy and the like, in addition to abnormal mottled calcification of cartilage, in some cases. Thus, it has been suggested that EBP plays an important role in bone growth and the like.

Emopamil (α-(1-methylethyl)-α-[3-[methyl(2-phenylethyl)amino]propyl]benzeneacetonitrile) has been known as an EBP ligand. It has been reported that compounds binding to EBP also have high affinity for calcium channel and other proteins such as a sigma-1 receptor. However, the pharmacological action of these compounds mediated by EBP has not yet been elucidated.

To date, alkyl ether derivatives, such as 1-(3-(2-(1-benzothiophen-5-yl)ethoxy)propylazetidin-3-ol, have been known to have neuroprotective action, nerve regeneration action, neurite outgrowth promoting action, and neurogenesis inducing action (Patent Documents 1 and 2). Moreover, such alkyl ether derivatives have also been known to exhibit high affinity for sigma receptors (Patent Document 3).

PRIOR ART DOCUMENTS

Patent Documents

Patent Document 1: International Publication WO03/035647
Patent Document 2: International Publication WO2007/125913
Patent Document 3: International Publication WO2016/199878

Non-Patent Documents

Non-Patent Document 1: Journal of Biological Chemistry, Vol. 271, pp. 22434-22440 (1996)
Non-Patent Document 2: Nature Genetics, Vol. 22, pp. 286-290 (1999)

SUMMARY OF INVENTION

Object to be Solved by the Invention

It has been desired to develop a compound having high affinity for EBP, and a method for activating or inhibiting EBP, using such a compound.

Means for Solving the Object

Under such circumstances, the present inventor has conducted intensive studies, and as a result, the inventor has found that an alkyl ether derivative represented by the following formula [1] or a salt thereof exhibits high affinity for EBP and thus, is useful as an EBP binding agent, thereby completing the present invention:

[Formula 1]

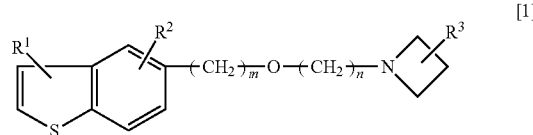

wherein $R^1$ and $R^2$, which are the same or different, each represent one or more groups selected from a hydrogen atom, a halogen atom, an optionally substituted $C_{1-6}$ alkyl group, an optionally substituted aryl group, an optionally substituted ar-$C_{1-6}$ alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group, and an oxo group; $R^3$ represents an optionally substituted $C_{1-6}$ alkylamino group, an optionally protected amino group, or an optionally protected hydroxyl group; and m and n, which are the same or different, each represent an integer of 1 to 6.

According to the present invention, the following inventions are provided.
(1) An EBP binding agent comprising the alkyl ether derivative represented by the formula [1] or a salt thereof.
(2) The EBP binding agent according to the above (1), wherein $R^1$ and $R^2$, which are the same or different, each represent a hydrogen atom, a halogen atom, or a $C_{1-6}$ alkoxy group.
(3) The EBP binding agent according to the above (1) or (2), wherein m is 2, and n is 2 or 3.
(4) The EBP binding agent according to any one of the above (1) to (3), wherein $R^3$ is an optionally protected hydroxyl group.

(5) The EBP binding agent according to the above (1), wherein the alkyl ether derivative is 1-(3-(2-(1-benzothiophen-5-yl)ethoxy)propylazetidin-3-ol.
(6) A method of using the alkyl ether derivative represented by the formula [1] or a salt thereof, to activate or inhibit EBP.
(7) The method according to the above (6), wherein $R^1$ and $R^2$, which are the same or different, each represent a hydrogen atom, a halogen atom, or a $C_{1-6}$ alkoxy group.
(8) The method according to the above (6) or (7), wherein m is 2, and n is 2 or 3.
(9) The method according to any one of the above (6) to (8), wherein $R^3$ is an optionally protected hydroxyl group.
(10) The method according to the above (6), wherein the alkyl ether derivative is 1-(3-(2-(1-benzothiophen-5-yl)ethoxy)propylazetidin-3-ol.

In addition, according to the present invention, the following inventions are also provided.
(a) Use of the alkyl ether derivative represented by the formula [1] or a salt thereof for the production of an EBP binding agent.
(b) A laboratory reagent comprising the alkyl ether derivative represented by the formula [1] or a salt thereof, which is for use in examining the physiological role and/or physiological activity of EBP.
(c) A reference material comprising the alkyl ether derivative represented by the formula [1] or a salt thereof, which is for use in examining the EBP activity of a sample.
(d) A method of using the alkyl ether derivative represented by the formula [1] or a salt thereof, for examining the physiological role and/or physiological activity of EBP.
(e) A method of using the alkyl ether derivative represented by the formula [1] or a salt thereof, for examining the EBP activity of a sample.

Advantageous Effects of Invention

The alkyl ether derivative represented by the formula [1] of the present invention or a salt thereof exhibits high affinity for EBP, and thus, is useful as an EBP binding agent.

The method of using the alkyl ether derivative represented by the formula [1] of the present invention or a salt thereof is useful as a method for activating or inhibiting EBP.

BRIEF DESCRIPTION OF DRAWINGS

FIG. 1 shows a comparison made between sigma-1 receptor-deficient cells and sigma-1 receptor-deficient and EBP-deficient cells, in terms of the radiation dose of tritium-labeled Compound A in the cells.

FIG. 2 shows a comparison made between sigma-1 receptor-deficient cells and sigma-1 receptor-deficient and EBP-overexpressing cells, in terms of the radiation dose of tritium-labeled Compound A in the cells.

EMBODIMENT OF CARRYING OUT THE INVENTION

Hereinafter, the present invention is described in detail.
In the present description, individual terms have the following meanings, unless otherwise specified.
The term "halogen atom" means a fluorine atom, a chlorine atom, a bromine atom, or an iodine atom.
The term "$C_{1-6}$ alkyl group" means a linear or branched $C_{1-6}$ alkyl group, such as a methyl, ethyl, propyl, isopropyl, butyl, isobutyl, tert-butyl, pentyl or hexyl group.
The term "$C_{2-6}$ alkenyl group" means a $C_{2-6}$ alkenyl group, such as vinyl, propenyl, butenyl, pentenyl or hexenyl.

The term "acyl $C_{1-6}$ alkyl group" means an acyl $C_{1-6}$ alkyl group, such as, for example, acetylmethyl, benzoylmethyl, p-nitrobenzoylmethyl, p-bromobenzoylmethyl, p-methoxybenzoylmethyl or 1-benzoylethyl.
The term "acyloxy $C_{1-6}$ alkyl group" means an acyloxy $C_{1-6}$ alkyl group, such as, for example, acetoxymethyl, propionyloxymethyl or pivaloyloxymethyl.
The term "arylthio $C_{1-6}$ alkyl group" means a group, such as, for example, phenylsulfenylmethyl or 2-(p-nitrophenylsulfenyl)ethyl.
The term "arylsulfonyl $C_{1-6}$ alkyl group" means an arylsulfonyl $C_{1-6}$ alkyl group, such as, for example, p-toluenesulfonylethyl.
The term "nitrogen-containing heterocyclic $C_{1-6}$ alkyl group" means a nitrogen-containing heterocyclic $C_{1-6}$ alkyl group, such as, for example, phthalimidemethyl or succinimidemethyl.
The term "$C_{3-8}$ cycloalkyl group" means a $C_{3-8}$ cycloalkyl group, such as, for example, cyclopropyl, cyclobutyl, cyclopentyl or cyclohexyl.
The term "$C_{1-6}$ alkylthio $C_{1-6}$ alkyl group" means a $C_{1-6}$ alkylthio $C_{1-6}$ alkyl group, such as, for example, methylthiomethyl, ethylthiomethyl or propylthiomethyl.
The term "$C_{1-6}$ alkoxy $C_{1-6}$ alkyl group" means a $C_{1-6}$ alkyloxy $C_{1-6}$ alkyl group, such as, for example, methoxymethyl or 1-ethxyethyl.
The term "ar-$C_{1-6}$ alkyloxy $C_{1-6}$ alkyl group" means an ar-$C_{1-6}$ alkyloxy $C_{1-6}$ alkyl group, such as, for example, benzyloxymethyl or phenethyloxymethyl.
The term "$C_{1-6}$ alkoxy group" means a linear or branched $C_{1-6}$ alkyloxy group, such as a methoxy, ethoxy, propoxy, isopropoxy, butoxy, isobutoxy, tert-butoxy, pentyloxy or hexyloxy group.
The term "$C_{2-6}$ alkenyloxy group" means a $C_{2-6}$ alkenyloxy group, such as a vinyloxy, propenyloxy, butenyloxy, pentenyloxy or hexenyloxy group.
The term "$C_{1-6}$ alkylthio group" means a $C_{1-6}$ alkylthio group, such as methylthio, ethylthio, propylthio, isopropylthio, butylthio, isobutylthio, tert-butylthio, pentylthio or hexylthio.
The term "aryl group" means a phenyl, naphthyl, indanyl or indenyl group.
The term "aryloxy group" means a phenyloxy, naphthyloxy, indanyloxy or indenyloxy group.
The term "ar-$C_{1-6}$ alkyl group" means an ar-$C_{1-6}$ alkyl group, such as a benzyl, diphenylmethyl, trityl or phenethyl group.
The term "arylthio group" means a phenylthio, naphthylthio, indanylthio or indenylthio group.
The term "acyl group" means a formyl group, a $C_{2-6}$ alkanoyl group such as acetyl, isovareryl, propionyl or pivaloyl, an ar-$C_{1-6}$ alkylcarbonyl group such as benzylcarbonyl, or an aroyl group such as benzoyl or naphthoyl.
The term "$C_{1-6}$ alkyloxycarbonyl group" means a linear or branched $C_{1-6}$ alkyloxycarbonyl group, such as, for example, methoxycarbonyl, ethoxycarbonyl, 1,1-dimethylpropoxycarbonyl, isopropoxycarbonyl, 2-ethylhexyloxycarbonyl, tert-butoxycarbonyl or tert-pentyloxycarbonyl.
The term "ar-$C_{1-6}$ alkyloxycarbonyl group" means an ar-$C_{1-6}$ alkyloxycarbonyl group, such as, for example, a benzyloxycarbonyl or phenethyloxycarbonyl group.
The term "aryloxycarbonyl group" means a group such as, for example, phenyloxycarbonyl.
The term "heterocyclic oxycarbonyl group" means a group such as, for example, 2-furfuryloxycarbonyl or 8-quinolyloxycarbonyl.

The term "$C_{1-6}$ alkylsulfonyl group" means a $C_{1-6}$ alkylsulfonyl group, such as, for example, methyl sulfonyl, ethylsulfonyl or propylsulfonyl.

The term "arylsulfonyl group" means a phenylsulfonyl, p-toluenesulfonyl or naphthylsulfonyl group, etc.

The term "$C_{1-6}$ alkylamino group" means a mono- or di-$C_{1-6}$ alkylamino group, such as methylamino, ethylamino, propylamino, isopropylamino, butylamino, dimethylamino, diethylamino, diisopropylamino or dibutylamino.

The term "heterocyclic group" means a 5- or 6-membered ring, condensed-ring or crosslinked-ring heterocyclic group comprising at least one heteroatom selected from nitrogen, oxygen or sulfur atoms, such as pyrrolidinyl, piperidinyl, piperazinyl, homopiperazinyl, homopiperidinyl, morpholyl, thiomorpholyl, tetrahydroquinolinyl, tetrahydroisoquinolinyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl and 1,4-benzodioxanyl groups.

The term "oxygen-containing heterocyclic group" means a group such as, for example, 2-tetrahydropyranyl or 2-tetrahydrofuranyl.

The term "sulfur-containing heterocyclic group" means a group such as, for example, tetrahydrothiopyranyl.

The term "substituted silyl group" means a group such as, for example, trimethylsilyl, triethylsilyl or tributylsilyl.

The term "$C_{1-6}$ alkylsilyl $C_{1-6}$ alkyl group" means a group such as, for example, 2-(trimethylsilyl)ethyl.

The amino-protecting group includes all groups that can be used as protecting groups for common amino groups, and examples of the amino-protecting group may include the groups described in W. Greene, et al., Protective Groups in Organic Synthesis, 4th edition, pp. 696-868, 2007, John Wiley & Sons, INC. Specific examples of the amino-protecting group may include an acyl group, a $C_{1-6}$ alkyloxycarbonyl group, an ar-$C_{1-6}$ alkyloxycarbonyl group, an aryloxycarbonyl group, an ar-$C_{1-6}$ alkyl group, a $C_{1-6}$ alkoxy $C_{1-6}$ alkyl group, an ar-$C_{1-6}$ alkyloxy $C_{1-6}$ alkyl group, an arylthio group, a $C_{1-6}$ alkylsulfonyl group, an arylsulfonyl group, and a substituted silyl group.

The hydroxyl-protecting group includes all groups that can be used as protecting groups for common hydroxyl groups, and examples of the hydroxyl-protecting group may include the groups described in W. Greene, et al., Protective Groups in Organic Synthesis, 4th edition, pp. 16-299, 2007, John Wiley & Sons, INC. Specific examples of the hydroxyl-protecting group may include an acyl group, a $C_{1-6}$ alkyloxycarbonyl group, an ar-$C_{1-6}$ alkyloxycarbonyl group, a heterocyclic oxycarbonyl group, a $C_{1-6}$ alkyl group, a $C_{2-6}$ alkenyl group, an ar-$C_{1-6}$ alkyl group, an oxygen-containing heterocyclic group, a sulfur-containing heterocyclic group, a $C_{1-6}$ alkoxy $C_{1-6}$ alkyl group, an ar-$C_{1-6}$ alkyloxy $C_{1-6}$ alkyl group, a $C_{1-6}$ alkylsulfonyl group, an arylsulfonyl group, and a substituted silyl group.

The carboxyl-protecting group includes all groups that can be used as protecting groups for common carboxyl groups, and examples of the carboxyl-protecting group may include the groups described in W. Greene, et al., Protective Groups in Organic Synthesis, 4th edition, pp. 533-643, 2007, John Wiley & Sons, INC. Specific examples of the carboxyl-protecting group may include a $C_{1-6}$ alkyl group, a $C_{2-6}$ alkenyl group, an aryl group, an ar-$C_{1-6}$ alkyl group, an acyl $C_{1-6}$ alkyl group, an arylthio $C_{1-6}$ alkyl group, an arylsulfonyl $C_{1-6}$ alkyl group, an oxygen-containing heterocyclic group, a $C_{1-6}$ alkylsilyl $C_{1-6}$ alkyl group, an acyloxy $C_{1-6}$ alkyl group, a nitrogen-containing heterocyclic $C_{1-6}$ alkyl group, a $C_{3-8}$ cycloalkyl group, a $C_{1-6}$ alkoxy$C_{1-6}$ alkyl group, an ar-$C_{1-6}$ alkyloxy $C_{1-6}$ alkyl group, a $C_{1-6}$ alkylthio $C_{1-6}$ alkyl group, and a substituted silyl group.

Substituents for the $C_{1-6}$ alkyl group, aryl group, ar-$C_{1-6}$ alkyl group, $C_{1-6}$ alkoxy group, aryloxy group, $C_{1-6}$ alkylthio group, arylthio group, $C_{2-6}$ alkenyl group, $C_{2-6}$ alkenyloxy group, $C_{1-6}$ alkylamino group, $C_{1-6}$ alkylsulfonyl group, arylsulfonyl group, carbamoyl group, and heterocyclic group, which are represented by $R^1$ and $R^2$, and the $C_{1-6}$ alkylamino group represented by $R^3$, may be selected from a halogen atom, a $C_{1-6}$ alkyl group, a $C_{3-8}$ cycloalkyl group, an aryl group, a $C_{1-6}$ alkoxy group, an aryloxy group, a $C_{1-6}$ alkylthio group, an arylthio group, a $C_{2-6}$ alkenyl group, a $C_{1-6}$ alkylsulfonyl group, an arylsulfonyl group, a $C_{1-6}$ alkylamino group, an optionally protected amino group, an optionally protected hydroxyl group, an optionally protected carboxyl group, an acyl group, a heterocyclic group, and the like.

Examples of the salt of the compound represented by the formula [1] may include the salts of generally known basic groups such as amino groups, or acidic groups such as hydroxyl or carboxyl groups.

Examples of the salts of basic groups may include: salts with mineral acids, such as hydrochloric acid, hydrobromic acid, nitric acid, and sulfuric acid; salts with organic carboxylic acids, such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids, such as methanesulfonic acid, benzenesulfonic acid, p-toluenesulfonic acid, mesitylenesulfonic acid, and naphthalenesulfonic acid.

Examples of the salts of acidic groups may include: salts with alkali metals, such as sodium and potassium; salts with alkaline earth metals, such as calcium and magnesium; ammonium salts; and salts with nitrogen-containing organic bases, such as trimethylamine, triethylamine, tributylamine, pyridine, N,N-dimethylaniline, N-methylpiperidine, N-methylmorpholine, diethylamine, dicyclohexylamine, procain, dibenzylamine, N-benzyl-β-phenethylamine, 1-ephenamine, and N,N'-dibenzylethylenediamine.

Among the above-described salts, preferred salts may include pharmacologically acceptable salts, and more preferred salts may include maleic acid.

When the alkyl ether derivative represented by the formula [1] or a salt thereof includes isomers (for example, optical isomers, geometrical isomers, tautomers, etc.), the present invention includes all of those isomers, and also include hydrates, solvates and various forms of crystals.

The alkyl ether derivative represented by the formula [1] or a salt thereof, which is used in the present invention, includes the following preferred compounds.

Preferable is a compound, in which $R^1$ is a hydrogen atom, a halogen atom, or a $C_{1-6}$ alkoxy group; and more preferable is a compound, in which $R^1$ is a hydrogen atom.

Preferable is a compound, in which $R^2$ is a hydrogen atom, a halogen atom, or a $C_{1-6}$ alkoxy group; and more preferable is a compound, in which $R^2$ is a hydrogen atom.

Preferable is a compound, in which $R^3$ is an optionally protected hydroxyl group; and more preferable is a compound, in which $R^3$ is a hydroxyl group.

Preferable is a compound, in which m is 2, and n is 2 or 3; and more preferable is a compound, in which m is 2, and n is 3.

The alkyl ether derivative represented by the formula [1] is particularly preferably 1-(3-(2-(1-benzothiophen-5-yl)ethoxy)propylazetidin-3-ol, and the salt thereof is particularly preferably maleate.

It can be expected that the present invention will be used in studies for elucidating the role of EBP in various physiological and pathological pathways.

The alkyl ether derivative represented by the formula [1] of the present invention or a salt thereof can be used as a laboratory reagent or a reference material in experiments regarding EBP activity. For example, the present alkyl ether derivative or a salt thereof can be used in purification of EBP fractions, screening for a novel EBP binding agent, activator or inhibitor, the imaging of EBP, etc.

When the alkyl ether derivative represented by the formula [1] of the present invention or a salt thereof is used in experiments, it can also be used by being dissolved in a solvent (for example, dimethyl sulfoxide, etc.). Moreover, the present alkyl ether derivative or a salt thereof can also be used together with an auxiliary agent (for example, a stabilizer, a pH adjuster, etc.) or other pharmaceutical components.

It can be expected that the present invention is used in the prevention and/or treatment of disease associated with EBP.

The drug characterized in that it comprises the alkyl ether derivative represented by the formula [1] of the present invention or a salt thereof can be used as a preventive and/or therapeutic agent against the disease associated with EBP.

The method comprising administering the alkyl ether derivative represented by the formula [1] of the present invention or a salt thereof to a subject can be used as a method for preventing and/or treating the disease associated with EBP.

The method for preventing and/or treating the disease associated with EBP may comprise measuring EBP activity in a subject, and then administering the alkyl ether derivative represented by the formula [1] of the present invention or a salt thereof to a subject in need of activation or inhibition of EBP.

The alkyl ether derivative represented by the formula [1] of the present invention or a salt thereof can be used in the production of a preventive and/or therapeutic agent against the disease associated with EBP.

Examples of the disease associated with EBP may include male EBP disorder with X linked dominant Conradi-Hunermann chondrodysplasia punctate, and disease associated with cholesterol biosynthesis pathway. Examples of the disease associated with cholesterol biosynthesis pathway may include neurodegenerative disease (Alzheimer's disease, Huntington's disease, Parkinson's disease, amyotrophic lateral sclerosis (ALS), Down's syndrome, etc.), multiple sclerosis, schizophrenia, Smith-Lemli-Opitz Syndrome, Lathosterolosis, and Desmosterolosis.

The alkyl ether derivative represented by the formula [1] or a salt thereof, which is used in the present invention, can be produced by applying known methods or appropriately combining the known methods with one another, or applying the method described in Patent Document 1.

The alkyl ether derivative represented by the formula [1] or a salt thereof, which is used in the present invention, can be processed into a pharmaceutical product preparation, such as an oral agent (a tablet, a capsule, a powder agent, a granule, a fine granule, a pill, a suspending agent, an emulsion, a liquid agent, a syrup, etc.), an injection, or eye drops, by adding to the present alkyl ether derivative or a salt thereof, various types of pharmaceutical product additives, such as an excipient, a binder, a disintegrator, a disintegration inhibitor, a caking/adhesion inhibitor, a lubricant, an absorption/adsorption carrier, a solvent, an extender, a tonicity agent, a solubilizer, an emulsifier, a suspending agent, a thickener, a coating agent, an absorption promoter, a gelatinization/coagulation accelerator, a light stabilizer, a preservative, a desiccant, an emulsification/suspension/dispersion stabilizer, a coloring inhibitor, a deoxygenation/oxidation inhibitor, a corrective/corrigent, a coloring agent, a foaming agent, a defoaming agent, a soothing agent, an antistatic agent, and a buffer/pH adjuster.

The above-described various types of drugs are formulated according to ordinary methods.

The solid preparation for oral use, such as a tablet, a powder agent, or a granule, may be prepared according to a common method, for example, using pharmaceutical additives for solid preparations, including: excipients, such as lactose, white sugar, sodium chloride, glucose, starch, calcium carbonate, kaoline, crystalline cellulose, anhydrous dibasic calcium phosphate, partially pregelatinized starch, corn starch, and alginic acid; binders, such as simple syrup, glucose solution, starch solution, gelatin solution, polyvinyl alcohol, polyvinyl ether, polyvinyl pyrrolidone, carboxymethyl cellulose, shellac, methyl cellulose, ethyl cellulose, sodium alginate, gum Arabic, hydroxypropylmethyl cellulose, hydroxypropyl cellulose, water, and ethanol; disintegrators, such as dry starch, alginic acid, agar powders, starch, crosslinked polyvinyl pyrrolidone, crosslinked carboxymethyl cellulose sodium, carboxymethyl cellulose calcium, and starch sodium glycolate; disintegration inhibitors, such as stearyl alcohol, stearic acid, cacao butter, and hydrogenated oil; caking/adhesion inhibitors, such as aluminum silicate, calcium hydrogen phosphate, magnesium oxide, talc, and silicic anhydride; lubricants, such as carnauba wax, light silicic anhydride, aluminum silicate, magnesium silicate, hydrogenated oil, hydrogenated vegetable oil derivatives, sesame oil, white beeswax, titanium oxide, dried aluminum hydroxide gel, stearic acid, calcium stearate, magnesium stearate, talc, calcium hydrogen phosphate, sodium lauryl sulfate, and polyethylene glycol; absorption promoters, such as quaternary ammonium salt, sodium lauryl sulfate, urea, and enzyme; absorption/adsorption carriers, such as starch, lactose, kaoline, bentonite, silicic anhydride, hydrous silicon dioxide, magnesium metasilicate aluminate, and colloidal silicic acid.

Furthermore, the tablet can be processed into a generally coated tablet, such as, for example, a sugar-coated tablet, a gelatin-coated tablet, a gastric coated tablet, an enteric coated tablet, and a water-soluble film-coated tablet, as necessary.

The capsule is prepared by mixing the present alkyl ether derivative or a salt thereof with the above-exemplified various types of pharmaceutical products, and then filling the mixture into a hard gelatin capsule, a soft capsule, or the like.

Otherwise, the above-described various types of liquid preparation additives, such as a solvent, an extender, a tonicity agent, a solubilizer, an emulsifier, a suspending agent, or a thickener, are used, and according to a common method, an aqueous or oily suspension, a solution, syrup, and an elixir can be prepared.

The injection may be prepared according to a common method, using pharmaceutical product additives for liquid preparations, for example, including: diluents, such as water, ethyl alcohol, macrogol, propylene glycol, citric acid, acetic acid, phosphoric acid, lactic acid, sodium lactate, sulfuric acid, and sodium hydroxide; pH adjusters and buffers, such as sodium citrate, sodium acetate, and sodium phosphate; stabilizers, such as sodium pyrosulfite, ethylenediaminetetraacetic acid, thioglycolic acid, and thiolactic acid; tonicity agents, such as common salt, glucose, mannitol, or glycerin; solubilizers, such as carboxymethyl cellulose sodium, propylene glycol, sodium benzoate, benzyl benzoate, urethane, ethanolamine, or glycerin; soothing agents, such as calcium gluconate, chlorobutanol, glucose, or benzyl alcohol; and local anesthetic.

The eye drops may be prepared according to a common method, by appropriately mixing the present alkyl ether derivative or a salt thereof with: preservatives, such as chlorobutanol, sodium dehydroacetate, benzalkonium chloride, cetylpyridinium chloride, phenethyl alcohol, methyl p-oxybenzoate, and benzethonium chloride; buffers, such as borax, boric acid and potassium dihydrogen phosphate; thickeners, such as methyl cellulose, hydroxyethyl cellulose, carboxymethyl cellulose, hydroxypropylmethyl cellulose, polyvinyl alcohol, carboxymethyl cellulose sodium, and chondroitin sulfate; solubilizers, such as polysorbate 80 and polyoxyethylene hydrogenated castor oil; stabilizers, such as sodium edetate and sodium bisulfite; and tonicity agents, such as sodium chloride, potassium chloride, and glycerin.

The administration method of the above-described preparation is not particularly limited, and it is determined, as appropriate, depending on the form of the preparation, patient's age, sex, and other conditions, and the degree of the symptoms of the patient.

The dose of the active ingredient (the alkyl ether derivative represented by the formula [1] or a salt thereof) of the above-described preparation is selected, as appropriate, depending on usage, patient's age and sex, the form of the disease, other conditions, and the like. In general, the alkyl ether derivative represented by the formula [1] or a salt thereof may be administered to an adult, at a daily dose of 0.1 to 1000 mg, once or divided over several administrations, and preferably, at a daily dose of 40 to 500 mg, once or divided over several administrations.

EXAMPLES

Hereinafter, the present invention is described in the following test example. However, the present invention is not limited thereto.

As a test substance, 1-(3-(2-(1-benzothiophen-5-yl)ethoxy)propyl)azetidin-3-ol (hereinafter referred to as "Compound A") was used.

Regarding such Compound A, a radioisotope-labeled Compound A and a non-labeled Compound A were used. As such a radioisotope-labeled Compound A, a tritium-labeled Compound A represented by the following formula [2] was used:

[Formula 2]

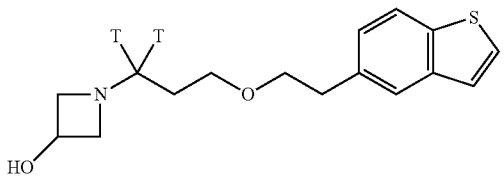

The tritium-labeled Compound A was prepared according to a common method, by adding tritiated lithium triethyl boron used as a tritium-labeling reagent to a compound represented by the following formula [3]:

[Formula 3]

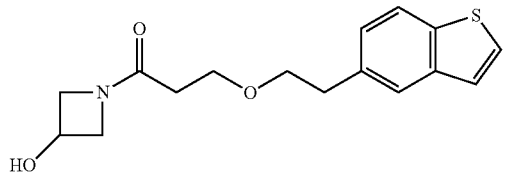

Test Example 1 (EBP Binding Test)

The binding ability of Compound A to EBP was examined. The test was carried out in accordance with Receptor Signal Transduction Protocols, pp. 135-164 (ISBN 978-1-61779-125-3).

A membrane fraction was collected from sigma-1 receptor-deficient human neuroblastoma (SH-SY5Y) cells, in which EBP was deleted or was overexpressed. Inactivated fetal bovine serum was added to a liquid medium DMEM (Dulbecco's Modified Eagle's Medium) to a final concentration of 10%, and then, a Penicillin-Streptomycin solution (10000 U/mL Penicillin-10000 μg/mL Streptmycin) was added to the medium to a final concentration of 100 U/mL Penicillin-100 μg/mL Streptmycin. The SH-SY5Y cells were cultured in the thus prepared medium.

The method of preparing a membrane fraction is as follows. The cells cultured to a subconfluent state were recovered using a cell scraper, and were then suspended in a 50 mM Tris-HCl (pH=7.4) buffer, followed by disintegrating the cells with an ultrasonic disintegrator. The disintegrated solution was centrifuged (1000 g, 10 minutes), and the supernatant was then ultracentrifuged (28000 rpm, 30 minutes). Thereafter, the obtained precipitate was re-suspended in a 50 mM Tris-HCl (pH=7.4) buffer to obtain a membrane fraction. Regarding the thus prepared membrane fraction, the protein concentration was measured according to a BCA method, and the membrane fraction was then adjusted to a concentration of approximately 1 mg/mL. Thereafter, as necessary, the membrane fraction was diluted with a 50 mM Tris-HCl (pH=7.4) buffer, which was then used in the subsequent test.

The receptor binding test method is as follows. A membrane fraction of individual cells (21.7 to 120 μg/well) and the tritium-labeled Compound A (0.05, 0.1, 0.2, 0.4, 0.8, 1.6, 3.1, 6.3, 12.5, 25.0, 50.0 or 100.0 nM) were added to a 96-well plate, and incubation was then carried out at 37° C. for 2 hours (Total binding). As a control, the tritium-labeled Compound A (0.05, 0.1, 0.2, 0.4, 0.8, 1.6, 3.1, 6.3, 12.5, 25.0, 50.0 or 100.0 nM) and the 100 μM non-labeled Compound A were added to a membrane fraction of individual cells, and incubation was then carried out in the same manner as described above (Non-specific binding). After completion of the incubation, the reaction solution was subjected to suction filtration with a 96-well glass filter, and the glass filter was then dried. Thereafter, a liquid scintillation cocktail was added thereto, and the radiation dose (CPM) in each well was then measured using a scintillation counter.

The specific binding ability of Compound A to EBP was determined by subtracting the radiation dose of the control (Non-specific binding) from the radiation dose derived from the tritium-labeled Compound A at each concentration (Total binding). Since the amount of the protein used was different depending on the cell membrane, CPM per μg of the membrane fraction protein used in the reaction was calculated (CPM/protein amount).

A comparison made between sigma-1 receptor-deficient cells and sigma-1 receptor-deficient and EBP-deficient cells, in terms of the radiation dose, is shown in FIG. 1.

A comparison made between sigma-1 receptor-deficient cells and sigma-1 receptor-deficient and EBP-overexpressing cells, in terms of the radiation dose, is shown in FIG. 2.

The radiation dose in the sigma-1 receptor-deficient and EBP-deficient cells was lower than the radiation dose in the sigma-1 receptor-deficient cells. In contrast, the radiation dose in the sigma-1 receptor-deficient and EBP-overexpressing cells was higher than the radiation dose in the sigma-1 receptor-deficient cells.

From these results, it became clear that Compound A has high affinity for EBP.

INDUSTRIAL APPLICABILITY

The alkyl ether derivative represented by the formula [1] of the present invention or a salt thereof exhibits high affinity for EBP, and is useful as an EBP binding agent.

The method of using the alkyl ether derivative represented by the formula [1] of the present invention or a salt thereof is useful as a method for activating or inhibiting EBP.

The invention claimed is:

1. A method for treating a disease associated with emopamil binding protein (EBP) which comprises administering an alkyl ether derivative represented by the following formula [1] or a salt thereof to a subject in need of activation or inhibition of EBP, wherein the disease associated with EBP is male EBP disorder with X linked dominant Conradi-Hunermann chondrodysplasia punctate, Smith-Lemli-Opitz Syndrome, Lathosterolosis, or Desmosterolosis,

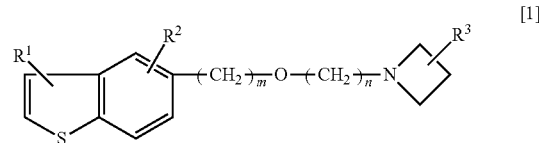

wherein $R^1$ and $R^2$, which are the same or different, each represents one or more groups selected from a hydrogen atom, a halogen atom, an optionally substituted $C_{1-6}$ alkyl group, an optionally substituted aryl group, an optionally substituted ar-$C_{1-6}$ alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, and a nitro group; $R^3$ represents an optionally substituted $C_{1-6}$ alkylamino group, an optionally protected amino group, or an optionally protected hydroxyl group; and m and n, which are the same or different, each represents an integer of 1 to 6.

2. The method according to claim 1, wherein $R^1$ and $R^2$, which are the same or different, each represents a hydrogen atom, a halogen atom, or a $C_{1-6}$ alkoxy group.

3. The method according to claim 1, wherein m is 2, and n is 2 or 3.

4. The method according to claim 1, wherein $R^3$ is an optionally protected hydroxyl group.

5. The method according to claim 1, wherein the alkyl ether derivative is 1-(3-(2-(1-benzothiophen-5-yl)ethoxy)propylazetidin-3-ol.

* * * * *